Figure 1:
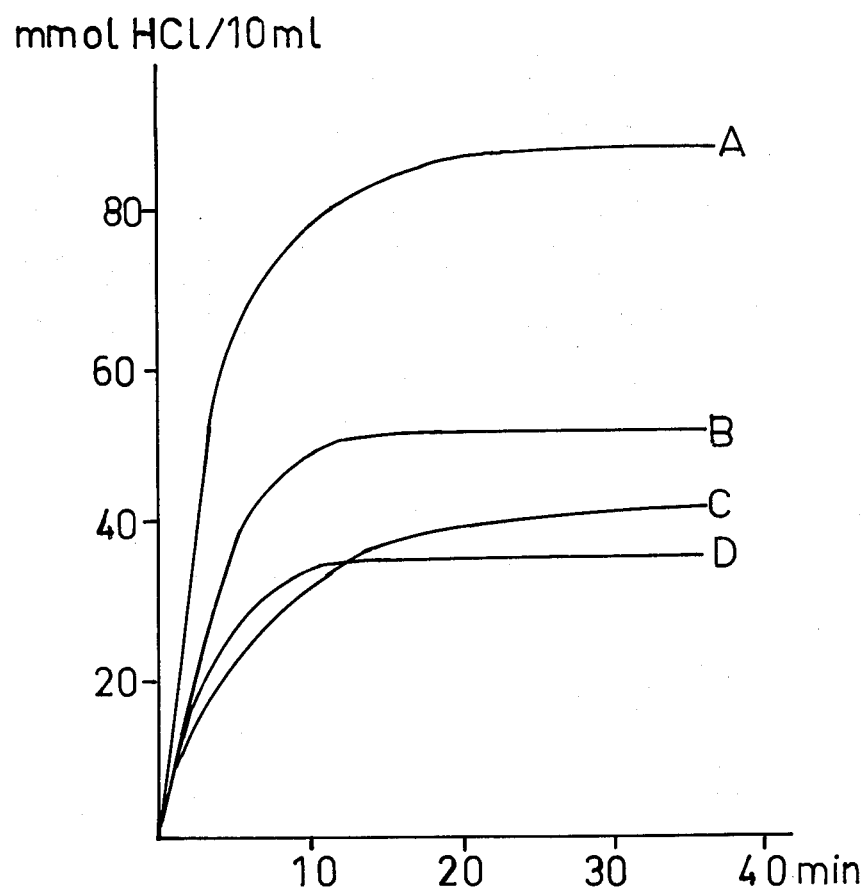

United States Patent [19]

Byröd et al.

[11] Patent Number: 4,465,667
[45] Date of Patent: Aug. 14, 1984

[54] PROCESS FOR THE PREPARATION OF GASTRIC ACID NEUTRALIZING AGENTS, GASTRIC ACID NEUTRALIZING AGENTS, AND A METHOD FOR TREATING HYPERACIDITY AND DISORDERS RELATED THERETO

[75] Inventors: Eva K. Byröd, Mölndal; John A. Sjögren, Mölnlycke, both of Sweden

[73] Assignee: Aktiebolaget Hässle, Mölndal, Sweden

[21] Appl. No.: 338,302

[22] Filed: Jan. 11, 1982

Related U.S. Application Data

[63] Continuation of Ser. No. 160,923, Jun. 19, 1980, abandoned.

[30] Foreign Application Priority Data

Jul. 9, 1979 [SE] Sweden ................................. 7905972

[51] Int. Cl.$^3$ .................... A61K 33/00; A61K 33/10; A61K 33/08
[52] U.S. Cl. .................................. 424/156; 424/127; 424/158
[58] Field of Search ....................... 424/157, 158, 156

[56] References Cited

U.S. PATENT DOCUMENTS

| | | | |
|---|---|---|---|
| 2,211,745 | 8/1940 | Stephenson | 424/157 |
| 2,999,790 | 9/1961 | Alford | 424/158 |
| 3,239,416 | 3/1966 | Rubino | 424/157 |
| 3,272,704 | 9/1966 | Beekman | 424/157 |
| 3,350,266 | 10/1967 | Granatek et al. | 424/157 |
| 3,499,963 | 3/1970 | Rubino | 424/157 |
| 3,599,150 | 8/1971 | Feinberg et al. | 424/157 |
| 3,873,694 | 3/1975 | Kanig | 424/157 |

FOREIGN PATENT DOCUMENTS 1414121 11/1975 United Kingdom ................ 424/157

OTHER PUBLICATIONS

Chemical Abstracts, 81: 123345w, (1974).
Chemical Abstracts, 88: 52223m, (1978).
Roquette Freres S.A. leaflet, Lycasin®, Jun. 1, 1976.
FASS® 1981 listing on Novaluzid®.

*Primary Examiner*—Frederick E. Waddell
*Attorney, Agent, or Firm*—Brumbaugh, Graves, Donohue & Raymond

[57] ABSTRACT

The present invention relates to gastric acid neutralizing compositions comprising dried aluminum hydroxide in suspension form, whereby the composition as suspension stabilizing and suspension forming agent comprises a hydrogenated, hydrolyzed glucose polymer in an amount of 2 to 30% by weight. By way of this content of the glucose polymer the amount of gastric acid neutralizing substance can be increased whereby smaller doses can be administered in obtaining gastric acid neutralization.

17 Claims, 1 Drawing Figure

PROCESS FOR THE PREPARATION OF GASTRIC ACID NEUTRALIZING AGENTS, GASTRIC ACID NEUTRALIZING AGENTS, AND A METHOD FOR TREATING HYPERACIDITY AND DISORDERS RELATED THERETO

This is a continuation of application Ser. No. 160,923 filed June 19, 1980, now abandoned.

The present invention relates to a process for the preparation of highly concentrated antacid suspensions comprising dried aluminum hydroxide, such antacid suspensions, and a method for the treatment of hyperacidity, and disorders related thereto, such as ulcers.

THE BACKGROUND OF THE INVENTION

Antacids are used to treat ulcers and for neutralizing an excess of acid such as a large production of gastric acid. The development of antacid therapy goes towards a use of large doses at frequent dosages to keep the amount of free acid in the stomach low during all the day and night. (Fordtran J et al.: N. Engl. J. Med. 288: 923–928, 1973; Fordtran J. et al.: N. Engl J. Med. 274; 921–927, 1966; Deering T, Mlagelada J-R: Gastroenterology 73: 11–14, 1977).

The requirements set forth on a complete antacid agent are i.a. that it shall have a high neutralizing capacity, rapid reaction with the hydrochloric acid of the gastric juice, have a maximal buffer capacity at pH 3 to 5, not give an increase of the pH of the stomach contents of above pH 7 at overdosage, not develop carbon dioxide in contact with hydrochloric acid, not be absorbed as such or in ion form, and, in other respects, be pharmacologically inactive and be well tolerated.

The antacid compounds which are normally used are the following:

Sodium bicarbonate $$NaHCO_3 + HCl \rightarrow NaCl + H_2O + CO_2$$

Sodium bicarbonate is a potent, absorbable antacidum. As it is absorbed to a great extent, it will give systemic effects and can change the acid-base balance of the body. As it moreover contains sodium it can give edema.

Calcium carbonate $$CaCO_3 + 2HCl \rightarrow CaCl_2 + H_2O + CO_2$$

At the administration of calcium carbonate about 10% is absorbed. The preparation is a potent antacidum but is not recommended due to the risk for hypercalcemia, kidney function reduction, and alkalosis at the administration of large amounts. Calcium will also give a so called "acid rebound effect".

Magnesium hydroxide $$Mg(OH)_2 + 2HCl \rightarrow MgCl_2 + 2H_2O$$

Magnesium hydroxide is a potent antacidum. It is absorbed in amounts up to about 10% which is, why it should not be given to patients suffering from serious kidney disorders. As magnesium compounds give rise to diarrhoea due to laxing effect, it is often combined with aluminum compounds which have an obstipating effect.

Aluminum hydroxide $$Al(OH)_3 + 3HCl \rightarrow AlCl_3 + 3H_2O$$

As indicated above aluminum can, in contrast to magnesium compounds, give obstipation. The advantages with Al(OH)$_3$ are that it is not absorbed and that the compound buffers at an optimal pH (about pH 4).

Among the many acid neutralizing compounds that exist, the choice for use as an antacidum is relatively restricted, primarily due to the risk for side effects at frequent use. A great many experts say that a combination of aluminum and magnesium compounds best satisfies the demands for an ideal antacidum. Such combinations are also present in most antacid products, today. A combination of this type is also deemed to be the best from a medicinal point of view with regard to a high capacity antacidum. It is, however, difficult with ingredients of this type to obtain an easily flowing, palatable product which simultaneously has a high capacity and reacts rapidly with acid.

Aluminum hydroxides are relatively instable and their reaction capability with acid vary strongly. Especially if one dries the aluminum hydroxide gels to a pulverulent product the reaction capability is considerably reduced and the reaction with acid goes slowly even if the total capacity in respect of the aluminum amount is the same as for liquid gels. Dried aluminum hydroxide gel thus normally has a restricted value as antacidum.

Magnesium hydroxide or carbonate have good reaction ability with acid also in dried form but cannot be used solely due to their laxing effects in high doses. They will also raise the pH of the ventricle to about 9, which is not desired. Aluminum hydroxide is stabilized in the presence of magnesium carbonate so that the mixture can be dried to a pulverulent product with remaining neutralizing properties. This type of co-dried combination has obtained a widespread use in the dominating antacid products in the Nordic countries.

A combination of aluminum and magnesium compounds is regarded, as mentioned above, to be the best and is used in many antacid preparations. The combination of Al-Mg gives less side-effects and better tolerance than each compound alone. One is restricted in the use of hydrogen carbonate and Ca-carbonate due to the negative effects.

Aluminum hydroxides can show very large quality differences. Certain aluminum hydroxides react rapidly with acid but high concentrated gels react slowly and dried gels react very often slowly (Sjögren, Farm. Revy. 62, 551, 1963). (Cf above). Magnesium carbonate has a stabilizing effect on aluminum hydroxide at the drying (cf above) U.S. Pat. No. 2,797,978) and co-dried gels of aluminum hydroxide and magnesium carbonate can be prepared having a good neutralizing ability. Such dried products have obtained great use in antacid products, especially tablets.

In antacid suspensions thus most often a combination of aluminum hydroxide gel and magnesium hydroxide or carbonate is used. In case the products are based on undried gels or co-dried gels of the above-mentioned types it is normally not possible to make them as concentrated as one should like to. This means that the patients are forced to take large volumes of the products to obtain the effect requested. In newly published works, where the ulcer healing effect of antacid products has been studied, the dosage is 30 ml 7 times a day. (Peterson W et al.: N Engl. J. Med. 297: 341–345, 1977;

Ippoliti A F et al.: Gastroenterology 74: 393–395, 1978). It is of course very difficult for the patients to follow such a dosage scheme and it is from a medicinal point of view desirable to reduce the volumes of the dosages.

If one should increase the concentration of aluminum hydroxide in known suspensions, the suspensions will become too viscous when the $Al_2O_3$-content is about 7%, if undried gels are used. If on the other hand the magnesium content should be increased then the viscosity is less influenced but the product will become too laxative, which is why thus one needs a certain balance between Al and Mg-contents in the product. If the suspensions should be prepared from pulverulent dried aluminum hydroxide-magnesium carbonate gels instead, one can reach a somewhat higher capacity without having an unacceptable viscosity. Such products are used to neutralize about 5 mmol of acid per ml. Especially suspensions based on dried gels give problems in that they give a coarse, unpleasant feeling in the mouth. Therefore thickening agents, sugars, or sugar alcohols are added. The suspensions are homogenized with a colloid mill (Permier Mill, Mannesmann a.o.) in order to crush the particle aggregates and the like and thereby provide a smooth feeling in the mouth.

In GB Patent Specification No. 1.414.121 it has been proposed to add hydrolyzed starch to magnesium magma containing antacid compositions. However, it has been shown that the starch hydrolyzate used (Malto dextrin) does not give an increased capacity, i.e. one cannot introduce more gastric acid neutralizing agents into such compositions, without seriously affecting the viscosity of the product. (Cf Example 8 below).

At lower concentrations the suspensions have a tendency to settle and to give a bottom sediment which is hard to shake up. This is usually anticipated by the addition of a consistency improving thickening agent.

Highly concentrated suspension of Al and Mg-hydroxides will form solid to semisolid gels instead, which cannot be poured out of a bottle. The systems are characteristically thixothropic and the strengths of the gels increase strongly at storage so that suspensions which form the beginning have been acceptable can after storage be impossible to use.

THE PRESENT INVENTION

The above drawbacks of known antacid suspensions have now surprisingly been eliminated by the present invention, which is characterized in that the suspension comprises as a suspension forming and stabilizing agent a hydrogenated, hydrolyzed glucose polymer in a concentration of 2 to 30% by weight, whereby the amount of aluminum hydroxide is 5 to 20% expressed as $Al_2O_3$.

According to a preferred embodiment the hydrogenated glucose polymer is present in a concentration of 5 to 15% by weight.

According to a further, preferred embodiment further gastric acid neutralizing agents as aluminum carbonate, magnesium hydroxide, magnesium carbonate, calcium carbonate magnesium oxide or sodium bicarbonate are present.

Another preferred embodiment of the invention is characterized in that one as gastric acid neutralizing agent adds aluminum hydroxide-magnesium carbonate co-dried gel.

A further, other preferred embodiment of the invention is characterized in that one as further suspension stabilizing and -forming agent adds a sugar alcohol as xylitol, mannitol, sorbitol or glycerol, or a mixture of sugar alcohols obtained at the preparation of xylitol, or a sugar such as glucose, maltose, fructose, or saccharose.

A further preferred embodiment of the invention is characterized in that the sugar alcohol (-mixture) is added in an amount of 3 to 10% by weight.

Another aspect of the invention relates to a gastric acid neutralizing suspension, an antacidum in the form of a suspension, comprising dried aluminum hydroxide as gastric acid neutralizing agent, which suspension is characterized in that it as a suspension stabilizing and suspension forming compound comprises a hydrogenated, hydrolyzed glucose polymer in an amount of 2 to 30% by weight calculated on the suspension, gastric acid neutralizing aluminum hydroxide corresponding to 5 to 20% by weight of $Al_2O_3$, and water, and possibly preserving and flavoring agents.

A further aspect of the invention relates to a method for neutralizing an excess of hydrochloric acid in gastric juice of mammals, including man, for the treatment of hyperacidity and disorders related thereto, which method is characterized in that a therapeutical gastric acid neutralizing amount of a suspension comprising as neutralizing agent a dried aluminum hydroxide in an amount corresponding to 5 to 20% by weight of $Al_2O_3$, and as suspension stabilizing and suspension forming compound a hydrogenated, hydrolyzed glucose polymer in an amount of 2 to 30% by weight, and water, and possibly preserving and flavoring agents, is administered.

DISCLOSURE OF THE INVENTION

In attempts to manufacture high capacity antacidum based on dried aluminum hydroxide gels it has been shown that a vehicle which comprises a hydrogenated glucose polymer (Lycasin®); Roquette Frères S. A., Lille, France, gives a possibility to obtain considerably more highly concentrated suspensions than if only water or traditional sugars or sugar alsohols, as sorbitol, are used.

Active ingredients in products according to the invention are aluminum hydroxides, which are dried either as such or together with magnesium hydroxide or magnesium carbonate. Usually the products contain, besides aluminum hydroxide, also hydroxides or carbonates of magnesium and can moreover contain other gastric acid neutralizing substances as calcium carbonate, sodium bicarbonate among others. The concentration which can be obtained varies between which compounds besides aluminum hydroxide are present and which raw material quality and which particle size are used. As a maximum about 40% of dry ingredients can be present, but usually 25 to 35% is the interval practically used, which interval corresponds to an acid binding capacity of 8 to 13 mmol HCl/ml of suspension.

Lycasin ® is a trade mark for a hydrolyzed, hydrogenated glucose sirup manufactured from corn starch. Lycasin ® differs from glucose in that reducing end molecules in each molecule chain have been changed into sorbitol molecules. According to the invention 2 to 30% are used to give the desired viscosity, taste and consistency of the suspensions. In most cases 5 to 15% give an optimal effect.

Lycasin ® contains as a maximum 0.2% reducing sugars, about 10% sorbitol (monosaccharide alcohol), about 90% hydrogenated oligo- and polysaccharides, and gives in a solution a pH of 6 to 7. The viscosity of the sirup varies depending on the temperature and quality, whereby one quality has the viscosity of 18000 cps at 4° C. and 450 cps at 40° C.

Lycasin ® can be combined with other sugars as glucose, maltose, fructose, saccharose, and sugar alcohols as sorbitol, mannitol, xylitol, glycerol, or a mixture of sugar alcohols obtained at the manufacture of xylitol. Especially from a taste point of view this may be advantageous. Other traditional ingredients can of course be present in the composition, e.g. flavours, preserving agents etc.

The product according to the invention is prepared by suspending the active ingredients in an aqueous solution of hydrogenated glucose polymer and optionally further sugars, sugar alcohols, flavours etc. It is, however, also poasible to add one or more of the soluble ingredients after having prepared the suspension. The suspension must usually be homogenized and ground by means of a suitable equipment (e.g. a colloid mill, type Mannesmann, Premier Mill), in order to obtain a smooth and palatable product.

In a preferred embodiment of the invention the product comprises a co-dried gel of aluminum hydroxide and magnesium carbonate in a concentration corresponding to 10% $Al_2O_3$ and 3% MgO, hydrogenated glucose polymer 5 to 15%, and sorbitol 3 to 10%.

EXAMPLE 1

$Al(OH)_3$-$MgCO_3$, F-MA 11[(x)] 23.0 g
MgO 1.7 g
Lycasin ® 75% 71.5 g
Sorbitol 70% 5.0 g
Methylparabene 0.05 g
Flavour, peppermint 0.01 g
Water to 100 g
[(x)]*According to U.S. Pat. No.* 2,797,978

Preparation: The magnesium oxide is stirred into water and is allowed to stand for hydration about 24 hrs. A minor amount of water is saved for final adjustment of the weight. Into the magnesium oxide suspension the following ingredients are added in below given order:

Sorbitol
Lycasin ®
$Al(OH)_3$-$MgCO_3$

After careful stirring the preserving agent and flavour are added, whereupon the final weight is adjusted with water, and the suspension is ground in a colloid mill. Acid binding capacity: about 850 ml of 0.1M HCl per 10 ml. The consistency is smooth and easy flowing.

EXAMPLE 2

$Al(OH)_3$, dried (54% $Al_2O_3$) 17.5 g
$Mg(OH)_2$, paste (22.6% MgO) 14.8 g
Lycasin ® 75% 20.0 g
Methylparabene 0.05 g
Flavour, lemon 0.06 g
Water to 100 g The suspension is prepared according to the same method as described in Ex. 1 above. Acid binding capacity: 850 ml of 0.1M HCl per 10 ml.

If Lycasin ® is replaced by water in the above composition then a suspension is obtained which already after one week is impossible to shake up, while a suspension containing Lycasin ® is very easy flowing after shaking.

EXAMPLE 3

$Al(OH)_3$-$MgCO_3$, F-MA 11 27 g
Lycasin ® 75% 20 g
Propylparabene 0.02 g
Methylparabene 0.02 g
Flavour, peppermint 0.01 g
Water to 100 g Acid binding capacity: about 890 ml of 0.1M HCl per 10 ml. This suspension is very easily shaken up after storage for one week. If Lycasin ® is replaced by sorbitol 75%, however, a suspension is obtained which is completely impossible to shake up.

EXAMPLE 4

$Al(OH)_3$-$MgCO_3$, F-MA 11 32 g
$CaCO_3$ 3 g
Lycasin ® 75% 17 g
Methylparabene 0.06 g
Flavour, orange 0.04 g
Water to 100 g Acid binding capacity: about 1150 ml of 0.1M HCl per 10 ml. If Lycasin ® is replaced by water in the above composition it will on the whole become impossible to produce the suspension as it becomes totally solid. If Lycasin ® is replaced by sorbitol a suspension is obtained which after 2 weeks of storage is very difficult to shake up.

EXAMPLE 5

$Al(OH)_3$ dried (54% $Al_2O_3$) 19 g
$MgCO_3$ 8 g
Sorbitol 70% 5 g
Lycasin ® 75% 10 g
Propylparabene 0.06 g
Flavour, lemon 0.05 g
Water to 100 g Acid binding capacity: 910 ml of 0.1M HCl per 10 ml. If Lycasin ® is replaced by sorbitol in the above composition a suspension is obtained which is very difficult to shake up after storage.

EXAMPLE 6

Aluminum hydroxid pulverulent (55% $Al_2O_3$) 15 g
Magnesium carbonate 7 g
Lycasin ®, pulverulent (100%) 30 g
Methylparabene 0.1 g
Flavour, peppermint 0.01 g
Water to 100 g The suspension was prepared according to Ex. 1. Capacity: 730 ml of 0.1M HCl per 10 ml of suspension. The suspension was relatively thick flowing but did not harden in 24 hrs.

EXAMPLE 7

$Al(OH)_3$ (55% $Al_2O_3$) powder 15.8 g
$MgCO_3$ 7.0 g
Saccharose 5.0 g
Lycasin ® 75% 2.7 g
Methylparabene 0.1 g
Flavour, peppermint 0.01 g
Water to 100 g The suspension was prepared in accordance with Ex. 1 above. The suspension is flowing, while a corresponding suspension without Lycasin ® gives a solid gel already after 24 hrs.

EXAMPLE 8

$Al(OH)_3$-$MgCO_3$, F-MA 11 25 g
Lycasin ® 100% 15 g
Methylparabene 0.05 g

Flavour, peppermint 0.01 g
Water to 100 g

Acid binding capacity: about 825 ml of 0.1M HCl per 10 ml. The suspension is easily shaken up after storage for one week. If Lycasin®️ in this composition is replaced by the same amount of lactose, saccharose or a starch hydrolysate Maltodextrin MD 02 (cf GB Patent Specification No. 1.414.121) suspensions are obtained, which are semisolid and which cannot be poured out of a bottle.

EXAMPLE 9

Aluminum hydroxide, dried gel 25 g
Lycasin®️ 75% 27 g
Methylparabene 0.05 g
Flavour, peppermint 0.01 g
Water to 100 g Acid binding capacity: 775 ml of 0.1M HCl per 10 ml. The suspension is easily flowing.

Pharmaceutical Effects

Antacid compositions create their effect by neutralizing the hydrochloric acid of the gastric juice. For a good product one must then require that it reacts rapidly with acid and has an acid neutralizing capacity enough to take care of the gastric juice which is secreted during the period the product is present in the stomach so that pH is increased at least above pH 3. Further it is required that it does not provide expressed side-effects (intoxications, obstipation, secondary acid secretion etc.) and that it is palatable enough so that the patient shall be able to follow dosage prescriptions.

In modern ulcer therapy using antacid compositions the trend is to utilize higher doses to achieve a safe effect for the main part of the patients. This means not only a frequent dosage but also an intake of large volumes of suspension or a great number of tablets (cf Table 1 below). The risk is then great that the patients are not able to follow the recommended dosage scheme, i.e. bad patient compliance. From a pharmaceutical point of view thus a high capacity antacidum should already in a dose of 10 ml neutralize 85 mmol hydrochloric acid. Another important aspect is that the product is able to rapidly neutralize the excess of acid in the stomach.

TABLE 1

An approximative dose of some antacid compositions for an acid neutralizing capacity corresponding to

|  | 50 | 80 | 150 mmol HCl |
|---|---|---|---|
| Novalucol ®️ susp. | 15 | 23 | 43 ml |
| Novalucol ®️ Forte susp. | 10 | 15 | 29 " |
| Camalox ®️ susp. | 14 | 22 | 42 " |
| Fosfalugel ®️ | 85 | 135 | 250 " |
| Novalvcol ®️ tabl. | 4 | 6 | 12 tablets |
| Camalox ®️ | 3 | 4.5 | 8 " |
| Altacet ®️ | 4 | 6 | 12 " |
| Rennie ®️ N | 3 | 5 | 10 " |
| Talakt ®️ | 6 | 10 | 19 " |
| Gavisoon ®️ | 20 | 32 | 60 " |
| Acc. to present inv. Ex. 1 | 6 | 10 | 18 ml |

(Calculated on an acid binding test according to USP XIX)

Novalucol ®️ susp. contains per 100 ml: 6 g of aluminum hydroxide, and 2.5 g of magnesium hydroxide, and sorbitol and constituents.

Novalucol ®️ Forte susp. contains per 100 ml: 6.2 g of aluminum hydroxide, 3.8 g of magnesium hydroxide, 6.3 g of aluminum hydroxide-magnesium carbonate (gel F-MA 11 according to JAPA sci. ed. 49:191, 1960), sorbitol and constituents.

Novalucol ®️ tablet contains 0.45 g of aluminum hydroxide-magnesium carbonate (gel F-MA 11).

Camalox ®️ susp. contains per 100 ml: 3.3 g of aluminum hydroxide, 5 g of calcium carbonate, 4 g of magnesium hydroxide, and pured water and constituents.

Camalox ®️ tablet contains 0.172 g of aluminum hydroxide, 0.25 g of calcium carbonate, 0.2 g of magnesium hydroxide, and constituents.

Fosfalugel ®️ contains per 100 ml: 55 g of 20% AlPO$_4$, 15 g of saccharose, calcium sulphate, pectin and constituents.

Altacet ®️ tablet contains 0.5 g of hydrotalcit, mannitol, lactose, and constituents.

Rennie ®️N tablet contains 0.68 g of calcium carbonate, 80 mg of magnesium carbonate and 0.475 g of constituents.

Talakt ®️ tablet contains 0.36 g of sodium hydroxy aluminum carbonate-sorbitol complex and constituents.

Gaviscon ®️ contains per tablet 0.35 g of alginic acid, 0.1 g of aluminum hydroxide, 0.12 g of sodium bicarbonate and constituents.

A composition according to the present invention containing an aluminum hydroxide-magnesium carbonate gel corresponding to 110 mg Al$_2$O$_3$ and 40 mg MgO per ml was compared with reference to acid binding capacity with three other antacid suspensions present on the market at pH 3 according to Sjögren, Farm Revy 62, 551, (1963).

A is a composition according to the invention as above, B is the composition Novalucol ®️ Forte susp. as defined above, D is the composition Novalucol ®️ as defined above, and C is a composition which per 100 g contains 8.6 g of aluminum hydroxide, 1.7 g of calcium carbonate, sorbitol, water and constituents (the composition C is sold under the Trade Mark Uracid ®️ by Aktiebolaget Hässle, Göteborg, Sweden). The results and the test are evident from Table 2 and FIG. 1.

TABLE 2

| Composition | Acid binding capacity mmol HCl per 10 ml of susp. after | | |
|---|---|---|---|
|  | 5 | 10 | 30 min. |
| A | 65 | 79 | 85 |
| B | 38 | 49 | 52.5 |
| C | 29 | 34 | 35 |
| D | 25 | 32 | 41 |

As evident from Table 1, Table 2, and FIG. 1, a suspension according to the present invention is a high capacity suspension, which in small or tolerably large doses, if so requested, gives an acceptable acid neutralizing effect.

In medical use of a composition according to the present invention, especially according to Ex. 1, the dose can dependent on the individual conditions of the patients vary from 5 to about 20 ml to be taken 3 to 8 times per day.

We claim:

1. A gastric acid neutralizing suspension comprising (i) a hydrogenated, hydrolyzed glucose polymer in an amount of 2 to 30% by weight, calculated on the suspension, as a suspension stabilizing and suspension forming agent, (ii) dried aluminum hydroxide corresponding to 5 to 20% by weight of Al$_2$O$_3$ as an acid neutralizing agent, (iii) water and (iv) optional preserving agents and flavorants.

2. The gastric acid neutralizing suspension according to claim 1, which suspension includes at least one other gastric acid neutralizing agent selected from the group consisting of sodium bicarbonate, calcium carbonate, magnesium carbonate, magnesium hydroxide, magnesium oxide and aluminum carbonate.

3. The gastric acid neutralizing suspension according to claim 1, wherein said aluminum hydroxide is in the form of a co-dried gel with magnesium carbonate.

4. The gastric acid neutralizing suspension according to claim 1, which suspension includes sugar alcohol selected from the group consisting of xylitol, mannitol, sorbitol, glycerol and a mixture thereof.

5. The gastric acid neutralizing suspension according to claim 1, which suspension includes at least one sugar selected from the group consisting of glucose, maltose, fructose and saccharose.

6. The gastric acid neutralizing suspension according to claim 1, wherein the hydrogenated, hydrolyzed glucose polymer is 5 to 15% by weight of the suspension.

7. The gastric acid neutralizing suspension according to claim 1, wherein the hydrogenated, hydrolyzed glucose polymer contains as a maximum 0.2% reducing sugars, about 10% sorbitol and about 90% hydrogenated oligo- and polysaccharides, said suspension having a pH of 6 to 7.

8. The gastric acid neutralizing suspension according to claim 1, wherein the dried aluminum hydroxide is 7 to 20% by weight of $Al_2O_3$.

9. A gastric acid neutralizing suspension comprising (i) a hydrogenated, hydrolyzed glucose polymer in an amount of 5 to 15% by weight, calculated on the suspension, as a suspension stabilizing and suspension forming agent, (ii) an aluminum hydroxide-magnesium carbonate co-dried gel corresponding to 10% by weight of $Al_2O_3$ and 3% by weight of MgO, (iii) sorbitol in an amount of 3 to 10% by weight, (iv) water and (v) optional preserving agents and flavorants.

10. A method for neutralizing the excess hydrochloric acid in the gastric juices of mammals including man and for the treatment of hyperacidity and disorders related thereto, characterized in that a therapeutic amount of a gastric acid neutralizing suspension is administered, wherein said suspension comprises (i) a hydrogenated, hydrolyzed glucose polymer in an amount of 2 to 30% by weight, calculated on the suspension, as a suspension stabilizing and suspension forming agent, (ii) dried aluminum hydroxide corresponding to 5 to 20% by weight of $Al_2O_3$ as an acid neutralizing agent, (iii) water and (iv) optional preserving agents and flavorants.

11. The method according to claim 10, which suspension includes at least one other gastric acid neutralizing agent selected from the group consisting of sodium bicarbonate, calcium carbonate, magnesium carbonate, magnesium hydroxide, magnesium oxide and aluminum carbonate.

12. The method according to claim 10, which suspension includes aluminum hydroxide-magnesium carbonate co-dried gel.

13. The method according to claim 10, which suspension includes sugar alcohol selected from the group consisting of xylitol, mannitol, sorbitol, glycerol and a mixture thereof.

14. The method according to claim 10, which suspension includes sugar selected from the group consisting of glucose, maltose, fructose and saccharose.

15. The method according to claim 10, wherein the hydrogenated, hydrolyzed glucose polymer is 5 to 15% by weight of the suspension.

16. The gastric acid neutralizing suspension according to claim 10, wherein the dried aluminum hydroxide is 7 to 20% by weight of $Al_2O_3$.

17. A method of forming and stabilizing gastric acid neutralizing suspensions which comprises combining a hydrogenated, hydrolyzed glucose polymer in an amount of 2 to 30% by weight calculated on the suspension with dried aluminum hydroxide corresponding to 5 to 20% by weight of $Al_2O_3$ and adding water and optional preserving agents and flavorants.

* * * * *